United States Patent
Kristoffersen et al.

(10) Patent No.: US 7,022,074 B2
(45) Date of Patent: Apr. 4, 2006

(54) METHOD AND APPARATUS FOR GENERATING A MULTI-LEVEL ULTRASOUND PULSE

(75) Inventors: Kjell Kristoffersen, Oslo (NO); Hans Garmann Torp, Trondheim (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 179 days.

(21) Appl. No.: 10/459,850

(22) Filed: Jun. 12, 2003

(65) Prior Publication Data

US 2004/0254459 A1    Dec. 16, 2004

(51) Int. Cl.
*A61B 8/00* (2006.01)
(52) U.S. Cl. ...................... 600/437; 310/317
(58) Field of Classification Search ............. 600/437, 600/440, 443, 447, 458; 310/317–319
See application file for complete search history.

(56) References Cited

U.S. PATENT DOCUMENTS

| | | | |
|---|---|---|---|
| 5,706,819 A * | 1/1998 | Hwang et al. ............... 600/458 |
| 5,833,614 A * | 11/1998 | Dodd et al. .................. 600/447 |
| 5,913,823 A * | 6/1999 | Hedberg et al. ............. 600/443 |
| 6,135,963 A | 10/2000 | Haider | |
| 6,226,228 B1 | 5/2001 | Hossack et al. | |
| 6,432,055 B1 * | 8/2002 | Carp et al. ................... 600/437 |
| 2004/0039283 A1* | 2/2004 | Banjanin et al. ............ 600/437 |

* cited by examiner

*Primary Examiner*—Francis J. Jaworski
(74) *Attorney, Agent, or Firm*—Armstrong Teasdale LLP; Dean D. Small

(57) ABSTRACT

A method and apparatus for generating ultrasound pulses comprises producing a multi-level pulse sequence including a series of pulses. The series of pulses includes at least three pulses having three different amplitudes, respectively. The amplitudes are at least one of a positive non-zero voltage, a negative non-zero voltage, and an intermediate level voltage. The multi-level pulse sequence may be produced by a switch network having at least three different input voltage levels. The switch network outputs the multi-level pulse sequence at an output node to a transducer within a probe. Echo signals based on the series of pulses are received, and an ultrasound image is produced based on the received echo signals.

24 Claims, 9 Drawing Sheets

METHOD AND APPARATUS FOR
GENERATING A MULTI-LEVEL
ULTRASOUND PULSE

BACKGROUND OF THE INVENTION

The present invention relates to diagnostic ultrasound systems. In particular, the present invention relates to method and apparatus for generating an ultrasound pulse sequence for approximating desired transmit spectrums.

Ultrasound systems are used to generate diagnostic ultrasound images of many different tissue and systems within a body. However, the ultrasound signal is progressively attenuated as it travels deeper into the tissue. Certain signal waveforms, such as a Gaussian waveform, are desirable as the waveform maintains its spectrum even when experiencing frequency dependent attenuation caused by tissue. For example, echoes from liver tissue will exhibit a depth dependent downshift in the center frequency of the waveform. Depending upon the spectrum of the transmitted pulse, bandwidth may be lost in echoes originating from large depths. It is well known that Gaussian waveforms exhibit no such loss of bandwidth.

In the past, many ultrasound systems have used bipolar transmitters to generate the ultrasound pulses. These transmitters typically generate waveforms defined by a sequence of positive and negative pulses, such as a square wave, with no intermediate zero segments. Bipolar transmitters are inexpensive to make and simple to control, but have limitations in the spectrum of the pulses it can generate. Also pulse width modulation of bipolar waveforms has been used for acoustic power control. This is done by reducing the duration of all of the positive and negative pulses of the base bipolar transmit waveform by the same fraction while the frequency of the waveform is maintained by inserting zero-segments between the pulses. This reduces the amplitude of the transmitted pulse while not substantially changing its spectrum within the pass-band of the transducer. In the past, use of pulse width modulated waveforms of this type has been restricted to Color flow or PW Doppler operation in simultaneous (duplex or triplex) operation with B-mode imaging using regular bi-polar waveforms.

In transmit apodization, the transmit pulse amplitude is usually progressively reduced towards the edges of the array relative to the center of the array. This is done to reduce sidelobes of the transmitted beam. Therefore, progressive pulse width modulation has been used toward the edge of the array to reduce the apparent amplitude of the pulse without substantially changing its spectrum. However, in the past, the spectrum of the transmit apodized waveform was limited to that of conventional bi-polar waveforms (i.e., the waveform of the central part of the array was always a conventional bi-polar pulse with no intermediate zero segments). Thus, many desired signal waveforms could not be successfully approximated.

By way of example only, FIG. 15 illustrates a conventional pulser 170. The pulser 170 has two switches, switch $SW1_1$ 172 and switch $SW2_1$ 174. Positive high voltage $+V_1$ is provided to input 176, which is connected to one side of switch $SW_1$ 172. Negative high voltage $-V_1$ is provided to input 178, which is connected to one side of switch $SW2_1$ 174. A resistor 184 connected to ground 186 provides the ability to pull the waveform to ground when neither of the switches 172 and 174 are closed. A controller 180 controls the switches $SW1_1$ 172 and $SW2_1$ 174 to produce an output waveform on output 182. Unfortunately, the resistor 184 needs to be small to provide the short transition times required in pulse width modulation, which leads to high losses.

Other ultrasound systems have used a large number of voltage levels to produce pulse sequences approximating arbitrary signal waveforms, such as providing 32 different levels of voltage to approximate, for example, a Gaussian waveform. However, using multiple voltage supplies is expensive to implement. These types of transmitters also have low efficiency, and thus high power consumption. Therefore, the aforementioned systems are expensive and inefficient to implement and maintain.

Thus, a system and method are desired to produce output pulse sequences to approximate desired waveforms that addresses the problems noted above and others previously experienced.

BRIEF SUMMARY OF THE INVENTION

A method for generating ultrasound pulses comprising producing a multi-level pulse sequence including a series of pulses, and controlling an amplitude of each pulse to be one of at least a positive non-zero voltage, a negative non-zero voltage, and an intermediate level voltage. The intermediate level voltage is measured with respect to the positive and negative non-zero voltages.

A method for generating a diagnostic ultrasound image comprising producing a multi-level pulse sequence including a series of pulses. The series of pulses includes at least a positive pulse, a negative pulse, and an intermediate level. The intermediate level is different from the positive and negative pulses, and has a voltage level between the positive and negative pulses. The method also comprises receiving echo signals based on the series of pulses, and producing an ultrasound image based on the received echo signals.

An ultrasound pulser comprises input nodes configured to receive first, second and third voltage levels, an output node configured to be connected to an ultrasound transducer, and a switch network interconnecting the input and output nodes. The switch network produces a multi-level pulse sequence including a series of pulses at the output node. The series of pulses includes at least three pulses having three different amplitudes, respectively. The amplitudes are positive, negative, and intermediate levels, and the intermediate level is different from and between the positive and negative levels.

An ultrasound system comprises a transducer transmitting and receiving ultrasound signals to and from an area of interest, and a transmitter driving the transducer with a multi-level pulse sequence including a series of pulses. The series of pulses comprises at least three different amplitudes including at least a positive pulse, a negative pulse, and an intermediate level that is different from and between the positive and negative pulses. The system also includes a processor processing echo signals received by the transducer and an output outputting ultrasound information based on processed echo signals.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

Figure 1:
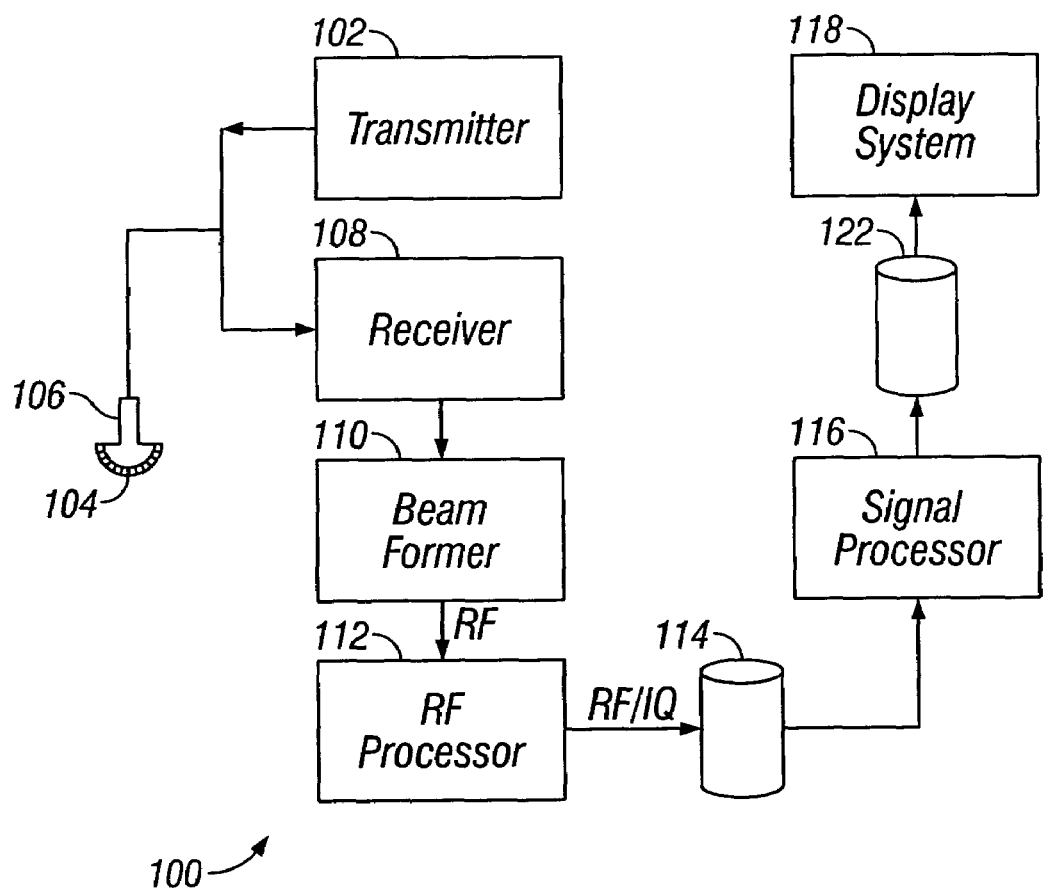
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives transducers 104 within a probe 106 to emit pulsed ultrasonic signals into a body. A variety of geometries may be used. The ultrasonic signals are back-scattered from structures in the body, like blood cells or muscular tissue, to produce echoes which return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information is displayed on the display system 118 at a slower frame-rate. An image buffer 122 is included for storing processed frames of acquired ultrasound information that are not scheduled to be displayed immediately. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 2:
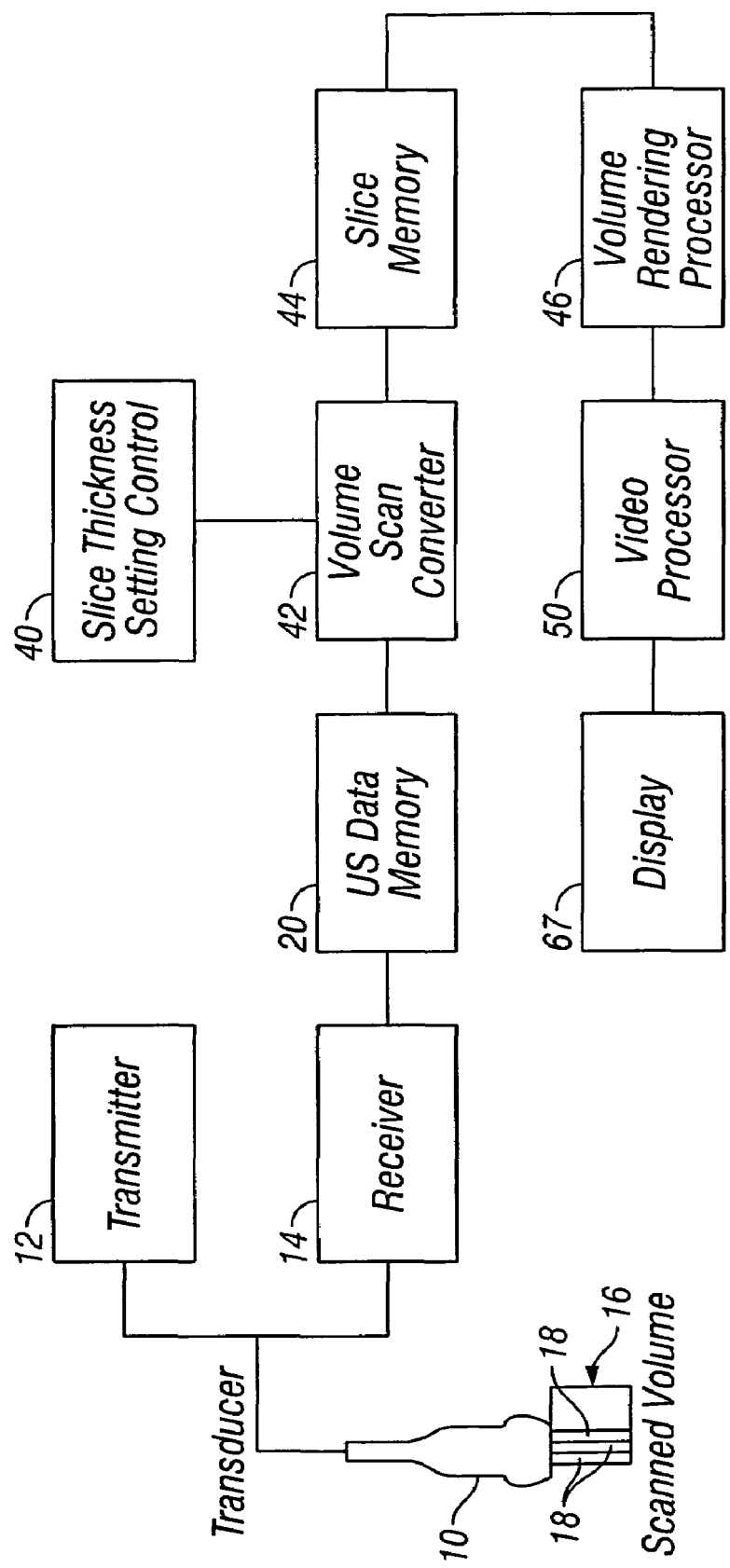
FIG. 2 illustrates an ultrasound system formed in accordance with one embodiment of the present invention.

FIG. 2 illustrates an ultrasound system formed in accordance with one embodiment of the present invention. The system includes a probe 10 connected to a transmitter 12 and a receiver 14. The probe 10 transmits ultrasonic pulses and receives echoes from structures inside of a scanned ultrasound volume 16. Memory 20 stores ultrasound data from the receiver 14 derived from the scanned ultrasound volume 16. The volume 16 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The transducer 10 is moved, such as along a linear or arcuate path, while scanning a region of interest (ROI). At each linear or arcuate position, the transducer 10 obtains scan planes 18. The scan planes 18 are collected for a thickness, such as from a group or set of adjacent scan planes 18. The scan planes 18 are stored in the memory 20, and then passed to a volume scan converter 42. In some embodiments, the transducer 10 may obtain lines instead of the scan planes 18, and the memory 20 may store lines obtained by the transducer 10 rather than the scan planes 18. The volume scan converter 42 may store lines obtained by the transducer 10 rather than the scan planes 18. The volume scan converter 42 receives a slice thickness setting from a control input 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by slice thickness control input 40. The data slice is stored in slice memory 44 and is accessed by a volume rendering processor 46. The volume rendering processor 46 performs volume rendering upon the data slice. The output of the volume rendering processor 46 is passed to the video processor 50 and display 67.

The position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

Figure 3:
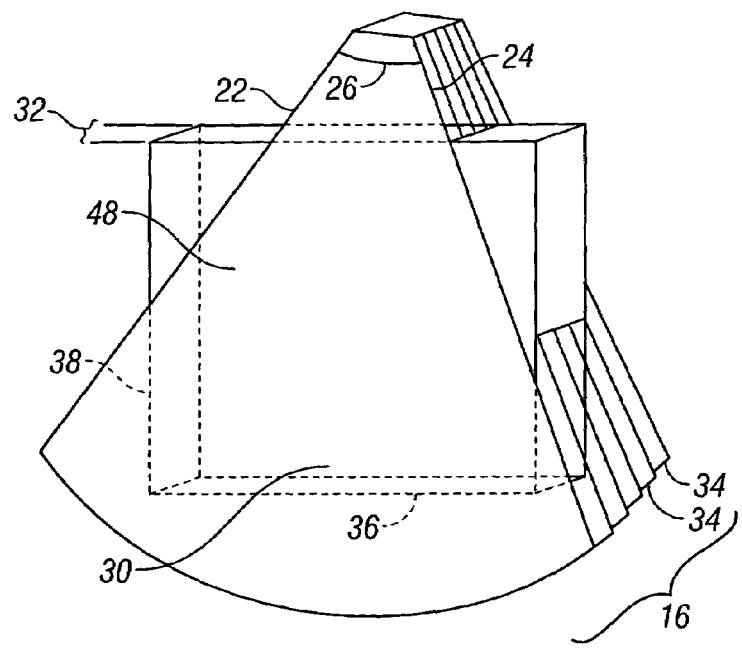
FIG. 3 illustrates a real-time 4D volume acquired by the system of FIG. 1 in accordance with one embodiment.

FIG. 3 illustrates a real-time 4D volume 16 acquired by the system of FIG. 1 in accordance with one embodiment. The volume 16 includes a sector shaped cross-section with radial borders 22 and 24 diverging from one another at angle 26. The probe 10 electronically focuses and directs ultrasound firings longitudinally to scan along adjacent scan lines in each scan plane 18 and electronically or mechanically focuses and directs ultrasound firings laterally to scan adjacent scan planes 18. Scan planes 18 obtained by the probe 10, as illustrated in FIG. 2, are stored in memory 20 and are scan converted from spherical to Cartesian coordinates by the volume scan converter 42. A volume comprising multiple scan planes is output from the volume scan converter 42 and stored in the slice memory 44 as rendering box 30 (FIG. 2). The rendering box 30 in the slice memory 44 is formed from multiple adjacent image planes 34.

The rendering box 30 may be defined in size by an operator to have a slice thickness 32, width 36 and height 38. The volume scan converter 42 may be controlled by the slice thickness control input 40 to adjust the thickness parameter of the slice to form a rendering box 30 of the desired thickness. The rendering box 30 designates the portion of the scanned volume 16 that is volume rendered. The volume rendered processor 46 accesses the slice memory 44 and renders along the thickness 32 of the rendering box 30.

During operation, a 3D slice having a pre-defined, substantially constant thickness (also referred to as the rendering box 30) is acquired by the slice thickness setting control 40 (FIG. 2) and is processed in the volume scan converter 42 (FIG. 2). The echo data representing the rendering box 30 may be stored in slice memory 44. Predefined thicknesses between 2 mm and 20 mm are typical, however, thicknesses less than 2 mm or greater than 20 mm may also be suitable depending on the application and the size of the area to be scanned. The slice thickness setting control 40 may include a rotatable knob with discrete or continuous thickness settings.

The volume rendering processor 46 projects the rendering box 30 onto an image portion 48 of an image portion 48 of an image plane 34 (FIG. 3). Following processing in the volume rendering processor 46, the pixel data in the image portion 48 may pass through a video processor 50 and then to a display 67.

The rendering box 30 may be located at any position and oriented at any direction within the scanned volume 16. In some situations, depending on the size of the region being scanned, it may be advantageous for the rendering box 30 to be only a small portion of the scanned volume 16.

Figure 4:
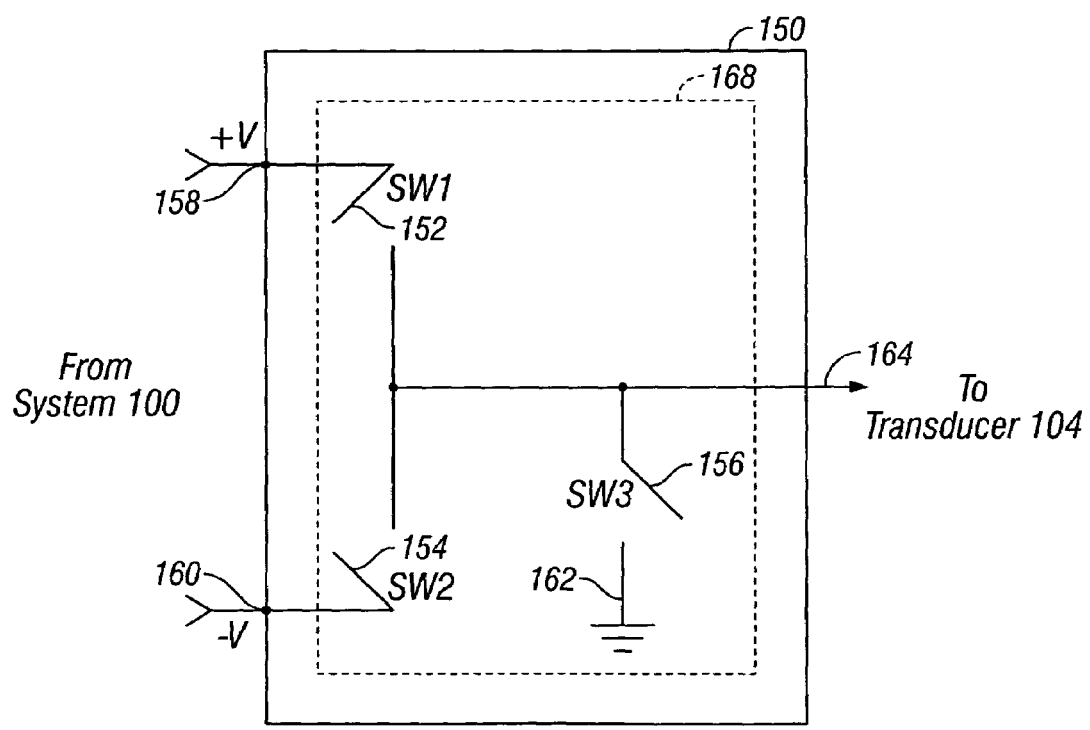
FIG. 4 illustrates a multi-level transmit pulser formed in accordance with an embodiment of the present invention.

FIG. 4 illustrates a multi-level pulser 150. By way of example, the multi-level pulser 150 may be included in the ultrasound probe 106 or the transmitter 102. The multi-level pulser 150 includes a tri-state switch network 168 comprising at least 3 switches, SW1 152, SW2 154, and SW3 156. Each switch, SW1 152, SW2 154, and SW3 156, may be an on/off switch, which has very low loss. It should be understood that other types of switches may be used.

The multi-level pulser 150 also includes three voltage inputs. Positive high voltage +V is connected to a first input node 158, which is connected to one side of switch SW1 152 in switch network 168. Negative high voltage −V is connected to a second input node 160, which is connected to one side of switch SW2 154 in switch network 168. Ground is connected to a third input node 162, which is connected to one side of switch SW3 156 in switch network 168. Alternatively, the input node 162 may be connected to an intermediate positive or negative voltage level different than, and between, the positive and negative high voltages connected to input nodes 158 and 160. The positive and negative high voltage levels may be supplied by the ultrasound system 100 high voltage power supply (not shown). An output node 164 provides an output signal to excite a transducer 104 in the probe 106.

Figure 5:
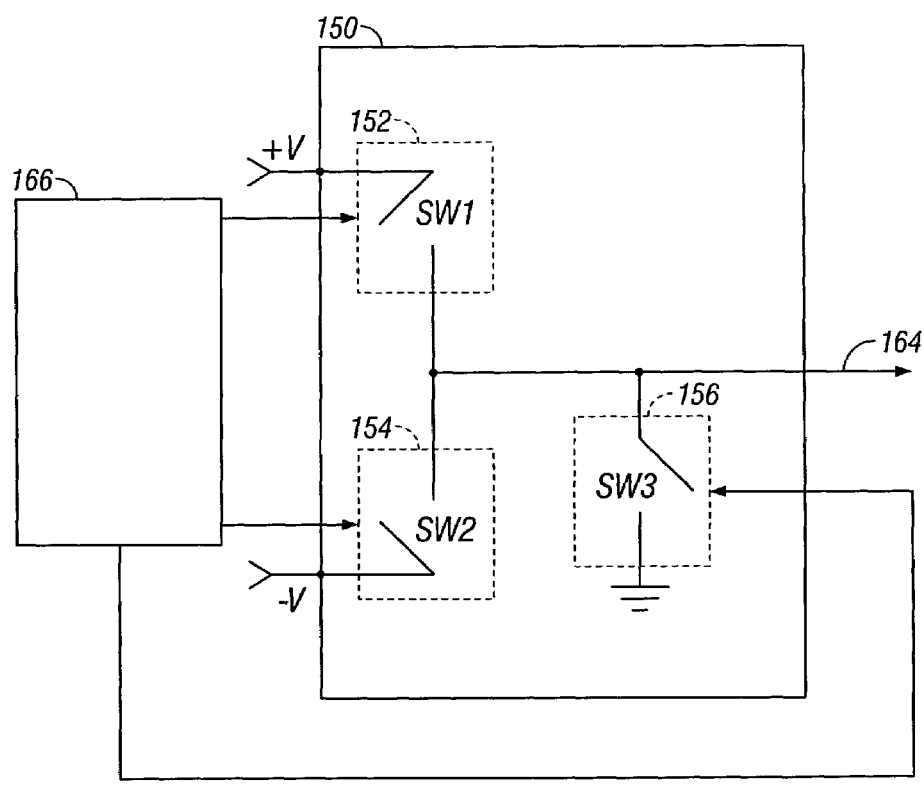
FIG. 5 illustrates the multi-level transmit pulser of FIG. 4 interconnected with a controller in accordance with an embodiment of the present invention.

FIG. 5 illustrates the multi-level pulser 150 of FIG. 4 interconnected with a controller 166. The controller 166 connects to and controls each of the switches SW1 152, SW2 154, and SW3 156. The controller 166 may be included in the transmitter 102 (FIG. 1) or may be located separately within the ultrasound system 100 or within another piece of hardware. If should be understood that the controller 166 may be implemented with either hardware or a combination of hardware and software.

The controller 166 controls the switches SW1 152, SW2 154, and SW3 156 within switch network 168 to produce a desired multi-level pulse sequence, which includes a series of at least two pulses and one intermediate third level. The multi-level pulse sequence is output to output node 164. Each transducer element 104 within the probe 106 may be driven by a separate multi-level pulser 150.

Figure 6:
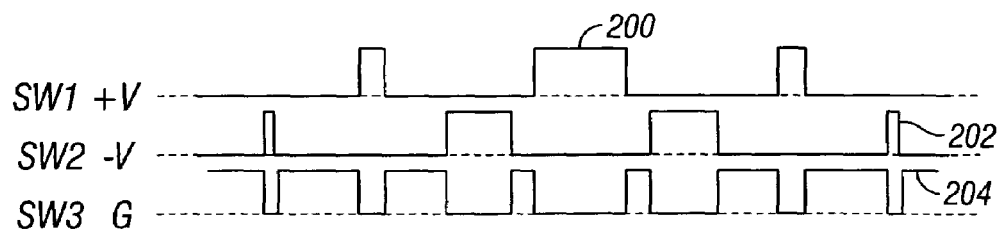
FIG. 6 illustrates three control waveforms using the pulser of FIG. 4 in accordance with an embodiment of the present invention.

FIG. 6 illustrates three control waveforms 200, 202, and 204. The controller 166 controls SW1 152, SW2 154 and SW3 156 to produce the control waveforms 200, 202 and 204, respectively. Precise control of the pulse widths within each of the control waveforms 200–204 is achieved by using the controller 166 and switches 152–156. For example, the controller 166 may control the pulse width in increments of 6.2 nsec, corresponding to a clock frequency of 160 MHz.

Figure 7:
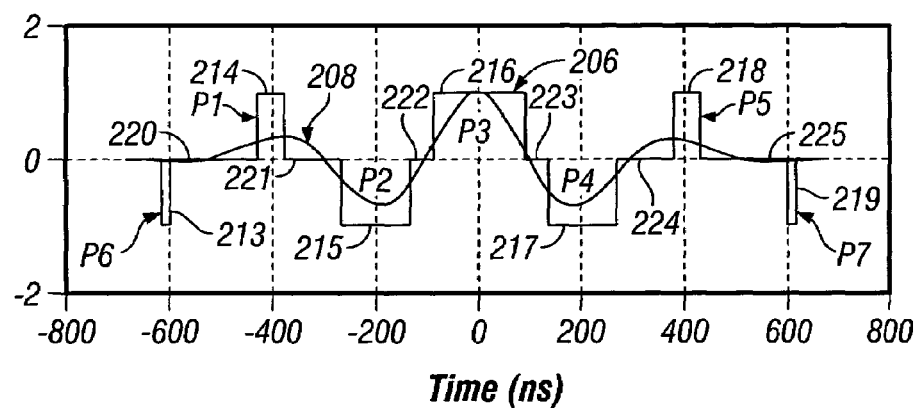
FIG. 7 illustrates a pulse width modulated firing sequence and a corresponding 60% fractional bandwidth Gaussian pulse using the multi-level pulser of FIGS. 4 and 5 in accordance with an embodiment of the present invention.
Figure 8:
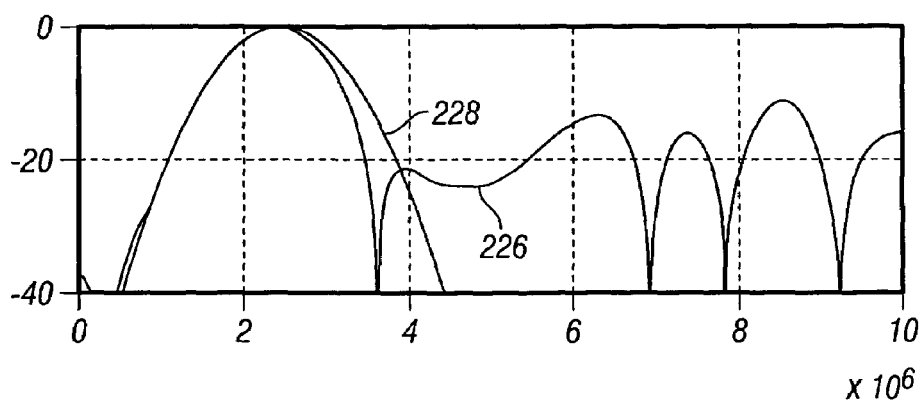
FIG. 8 illustrates spectras of the pulse sequence and Gaussian pulse of FIG. 7 in accordance with an embodiment of the present invention.

FIG. 7 illustrates a pulse width modulated firing sequence 206 and a corresponding 60% fractional bandwidth Gaussian pulse 208 using the multi-level pulser 150 of FIGS. 4 and 5. The pulse sequence 206 is symmetric. FIG. 8 illustrates spectras 226 and 228 of the pulse sequence 206 and Gaussian pulse 208, respectively. It should be noted that any spurious high-frequency components, such as may be introduced by the pulse sequence 206, will be filtered by the probe's 106 impulse response. Therefore, the spectras 226 and 228 are similar in terms of acoustic performance.

Pulse sequence 206 illustrates the resultant output waveform based on control waveforms 200–204 of FIG. 6. Pulse sequence 206 includes three different amplitude levels, as represented by +V, ground, and −V. It should be understood that if SW3 156 were connected to a different voltage level than ground, the third amplitude level would reflect the different intermediate voltage level.

Additionally, each pulse and intermediate voltage level in the pulse sequence 206 may be modulated to have a different width. For example, a first pulse may have a narrower pulse width and a first amplitude. A second pulse may have a wider pulse width and a second amplitude. A third pulse or intermediate voltage level may have a third amplitude and a width different from the first and second pulses, or may have a width the same as one of the first and second pulses.

In FIG. 7, pulses 213–219 and intermediate voltage levels 220–225 are illustrated. Pulse P1 214 is a positive, narrow pulse. Pulse P2 215 is a negative pulse, and is wider when compared to pulse P1 214. Pulse P3 216 is positive and wider than pulse P2 215. Pulses P6 213 and P7 219 are both negative, narrow pulses. As the pulse sequence 206 is symmetric, pulses P6 213 and P7 219 are equal, pulses P1 214 and P5 218 are equal, pulses P2 215 and P4 217 are equal, intermediate voltage levels 222 and 223 are equal, and intermediate voltage levels 221 and 224 are equal.

The multi-level pulser 150 and controller 166 provide precise control over the duration (or width) of pulses and the intermediate voltage levels 220–225, as discussed previously. Used in combination with the multiple amplitude levels, the output pulse sequences are produced to achieve the approximation of the desired transmit spectrum. For example, the length (number of cycles) of the overall pulse sequence depends upon the desired bandwidth. Long pulse sequences are used to approximate a Gaussian waveform with a narrow bandwidth, while shorter pulse sequences are used to approximate a Gaussian waveform with a wide bandwidth. The approximation of the desired transmit spectrum created by the multi-level pulser 150 and controller 166 achieves similar results as an analog pulser. However, the multi-level pulser 150 and controller 166 are much simpler, less expensive, consume less power and have a higher efficiency than an analog pulser.

FIGS. 9–13 illustrate other desired waveforms which may be approximated by using the controller 166 to control the switches SW1 152, SW2 154, and SW3 156 of the multi-level pulser 150. It should be understood that many other desired waveforms may be approximated and thus are not limited by FIGS. 9–13.

Figure 9:
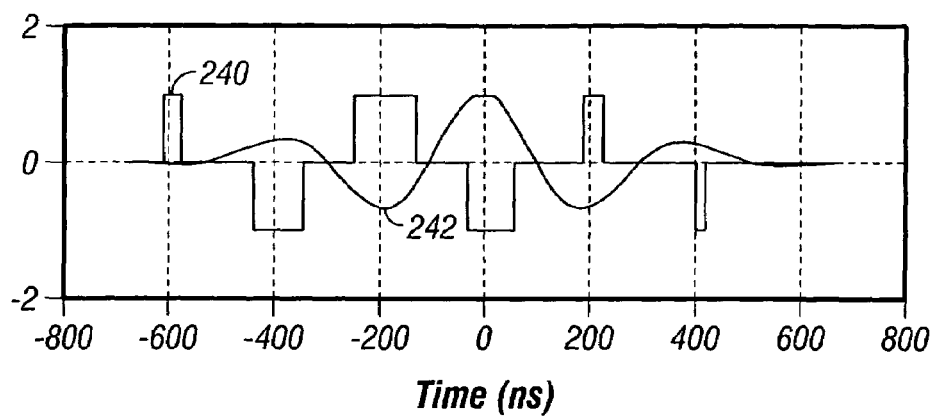
FIG. 9 illustrates a pulse width modulated firing sequence and a Gaussian pulse using the multi-level pulser of FIGS. 4 and 5 in accordance with an embodiment of the present invention.
Figure 10:
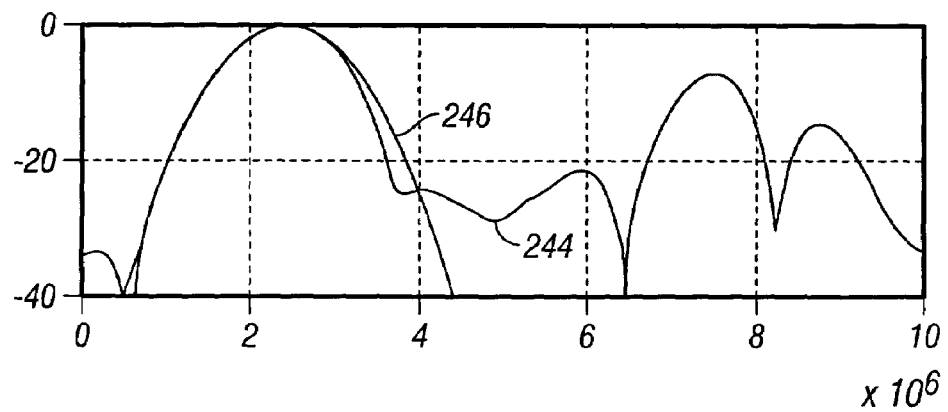
FIG. 10 illustrates spectras of the pulse sequence and Gaussian pulse of FIG. 9 in accordance with an embodiment of the present invention.

FIG. 9 illustrates a pulse width modulated firing sequence 240 and a Gaussian pulse 242 using the multi-level pulser 150 of FIGS. 4 and 5. The pulse sequence 240 is asymmetric. FIG. 10 illustrates spectras 244 and 246 of the pulse sequence 240 and Gaussian pulse 242, respectively. The spectral approximation is better with the asymmetric pulse sequence 240 in comparison to the symmetric pulse sequence 206 of FIG. 7.

Figure 11:
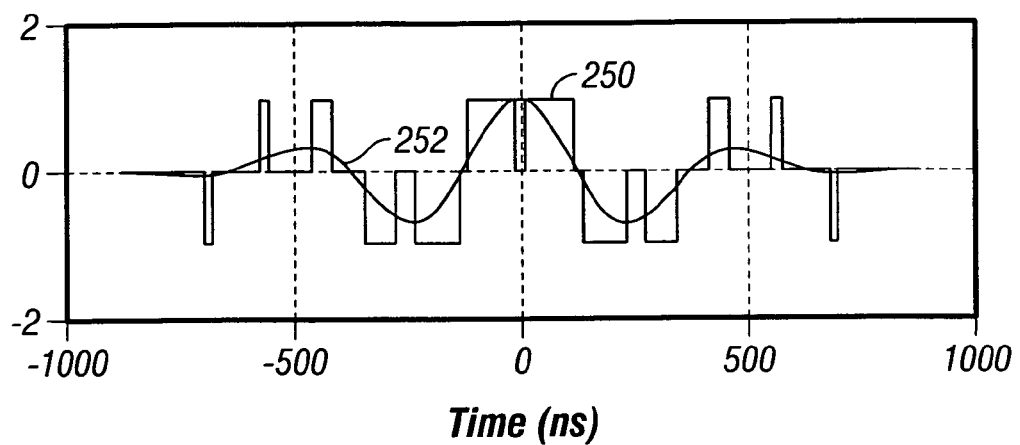
FIG. 11 illustrates a pulse width modulated firing sequence and a Gaussian pulse using the multi-level pulser of FIGS. 4 and 5 in accordance with an embodiment of the present invention.
Figure 12:
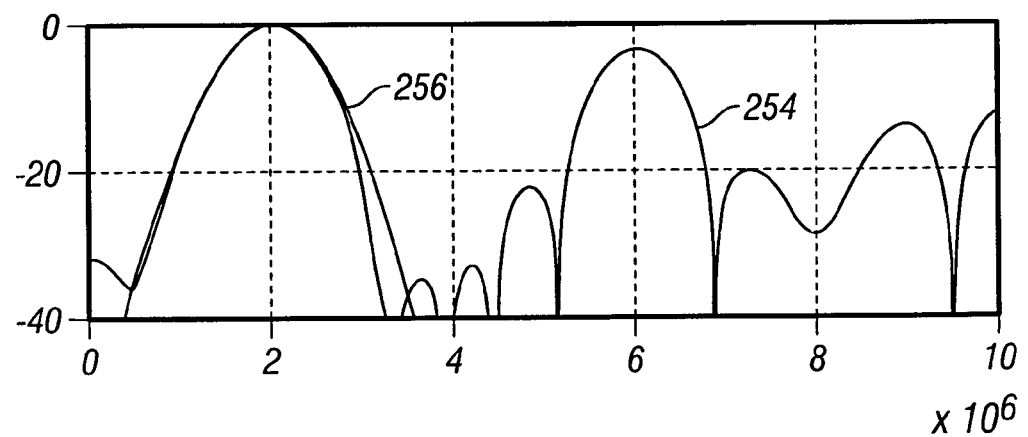
FIG. 12 illustrates spectras of the pulse sequence and Gaussian pulse of FIG. 11 in accordance with an embodiment of the present invention.

FIG. 11 illustrates a pulse width modulated firing sequence 250 and a Gaussian pulse 252 using the multi-level pulser 150 of FIGS. 4 and 5. FIG. 12 illustrates spectras 254 and 256 of the pulse sequence 250 and Gaussian pulse 252, respectively. Pulse sequence 250 is a higher-order pulse width modulated sequence and has approximately two pulses per half-period of the Gaussian waveform. The resulting spectrum approximation has low second harmonic contents.

Figure 13:
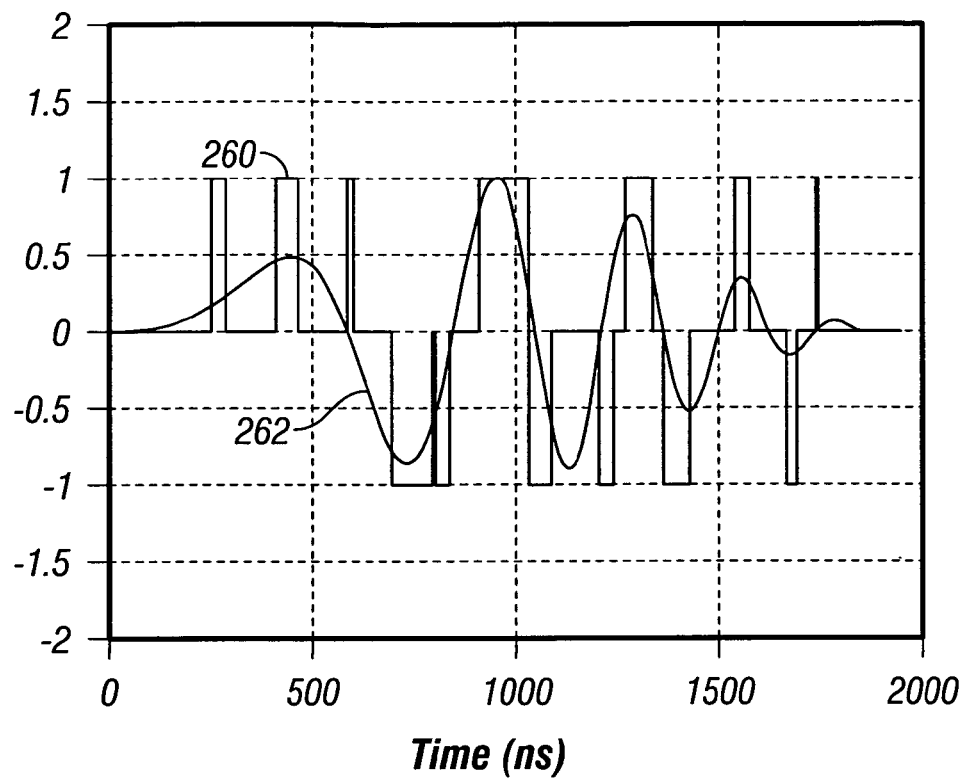
FIG. 13 illustrates a pulse width modulated firing sequence 260 and a weighted chirp waveform 262 using the multi-level pulser 150 of FIGS. 4 and 5 in accordance with an embodiment of the present invention.

FIG. 13 illustrates a pulse width modulated firing sequence 260 and a weighted chirp waveform 262 using the multi-level pulser 150 of FIGS. 4 and 5.

Figure 14:
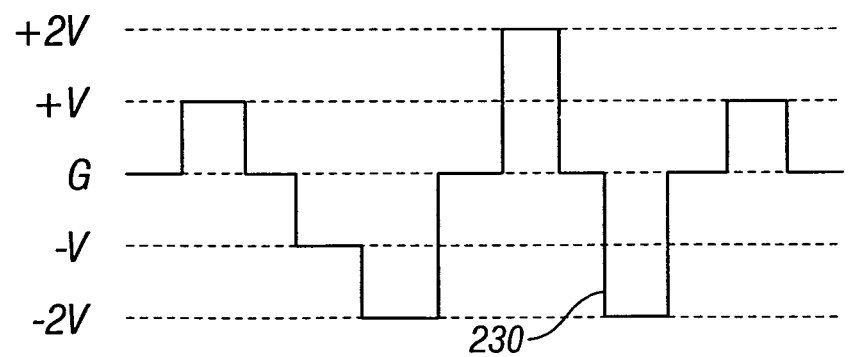
FIG. 14 illustrates a multi-level transmit pulse sequence in accordance with an embodiment of the present invention.
Figure 15:
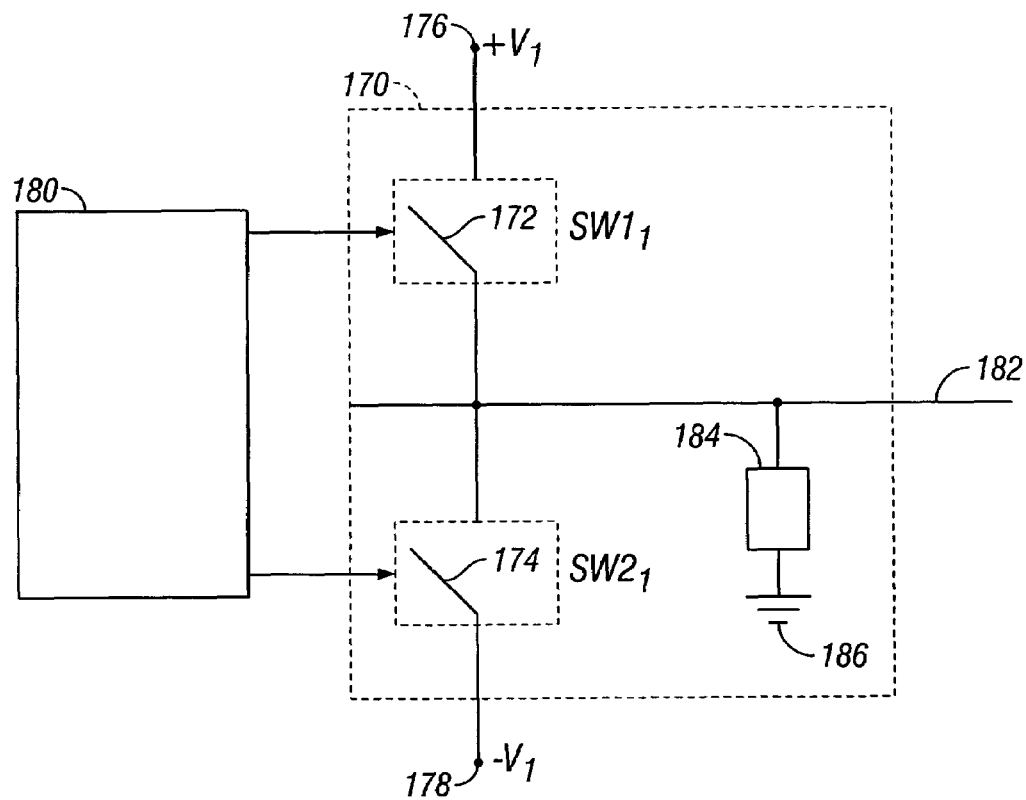
FIG. 15 illustrates a bi-polar pulser utilized by a conventional system.

FIG. 14 illustrates a multi-level transmit pulse sequence 230. In this example, the multi-level pulser 150 of FIG. 4 may be modified to include two additional switches. Two additional intermediate voltage levels, different with respect to the positive and negative high voltages, are also provided to two additional input nodes. The controller 166 controls the five switches to produce the transmit pulse sequence 230, including pulses and intermediate voltage levels having up to five different voltage levels. The pulse widths of each pulse and intermediate voltage level may be controlled by the controller 166 as previously discussed. It should be understood that additional pairs of switches may be added to the multi-level pulser 150 and controlled by the controller 166.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for generating ultrasound pulses, the method comprising:
   locating a switch network in an ultrasound probe;
   switching the switch network in the ultrasound probe to produce a multi-level pulse sequence including a series of pulses;
   controlling an amplitude of each pulse to be one of at least a positive non-zero voltage, a negative non-zero voltage, and an intermediate level non-zero voltage, said intermediate level non-zero voltage being between said positive and negative non-zero voltages; and
   modulating said series of pulses to approximate one of a Gaussian waveform and a chirp waveform.

2. The method of claim 1, further comprising controlling said series of pulses to include at least three pulses, each of which has a different amplitude.

3. The method of claim 1, further comprising modulating said series of pulses to include at least two different pulse widths.

4. The method of claim 1, further comprising modulating said series of pulses to include a narrow first pulse having a first amplitude, a wider second pulse having a second amplitude and a narrow third pulse having a third amplitude.

5. The method of claim 1, further comprising modulating said series of pulses within increments of 6.2 ns.

6. The method of claim 1, wherein the controlling step switches the amplitude between an odd number of different discrete amplitude levels.

7. A method for generating a diagnostic ultrasound image, the method comprising:
   locating a switch network in an ultrasound probe:
   switching the switch network in the ultrasound probe to produce a multi-level pulse sequence including a series of pulses, said series of pulses including at least a positive pulse, a negative pulse, and an intermediate level pulse, said intermediate level pulse being different from said positive and negative pulses, said intermediate level pulses, positive pulse and negative pulse being non-zero;
   modulating said series of pulses to include multiple pulse widths, said multiple pulse widths being produced with progressive pulse width modulation to approximate a desired waveform;
   receiving echo signals based on said series of pulses; and
   producing an ultrasound image based on said received echo signals.

8. The method of claim 7, further comprising modulating said series of pulses to include at least two different pulse widths.

9. The method of claim 7, further comprising modulating said series of pulses to approximate one of a Gaussian waveform and a chirp waveform.

10. The method of claim 7, said series of pulses beginning with said negative pulse.

11. The method of claim 7, said producing step further comprising producing said positive and negative pulses and said intermediate levels in an order to approximate a desired waveform.

12. The method of claim 7, further comprising switching said amplitude between an odd number of different discrete amplitude levels.

13. An ultrasound pulser configured to be located in an ultrasound probe, comprising:
   input nodes configured to receive first, second and third voltage levels from a transmitter external to the ultrasound probe;
   an output node configured to be connected to an ultrasound transducer; and
   a switch network, located in the ultrasound probe, interconnecting said input and output nodes, said switch network producing at said output node a multi-level pulse sequence including a series of pulses, said series of pulses including at least three pulses having three different amplitudes, respectively, said amplitudes being positive, negative, and intermediate levels, said intermediate level being different from and between said positive and negative levels and being a non-zero voltage.

14. The ultrasound pulser of claim 13, further comprising a controller controlling said switch network.

15. The ultrasound pulser of claim 13, further comprising at least three switches connected to said output node and to respective input nodes associated with said first, second and third voltage levels.

16. The ultrasound pulser of claim 13, further comprising at least three switches connected to said output node and to respective input nodes, each of said at least three switches closing at different times to drive said output node to a corresponding one of said three different amplitudes.

17. The ultrasound pulser of claim 13, further comprising a tri-state switch network interconnecting said input and output nodes.

18. The ultrasound pulser of claim 13, wherein said switch network modulates said series of pulses to include at least two different pulse widths.

19. The ultrasound pulser of claim 13, wherein said switch network modulates said series of pulses to include a narrow first pulse having a first amplitude, a wider second pulse having a second amplitude and an intermediate level having a third amplitude.

20. The ultrasound pulser of claim 13, wherein said switch network modulates said series of pulses to approximate one of a Gaussian waveform and a chirp waveform.

21. An ultrasound system, comprising:
   an ultrasound probe having a housing:
   a transducer, held in said housing of said probe, comprising an array of elements for transmitting and receiving ultrasound signals to and from an area of interest;
   a switch network, located in said housing of said probe, for driving said transducer with a multi-level pulse sequence including a series of pulses, said series of pulses comprising at least three different amplitudes, said three different amplitudes comprising at least a positive pulse, a negative pulse, and an intermediate level, said intermediate level being different from and between said positive and negative pulses;
   a processor for processing echo signals received by said transducer; and
   an output for outputting ultrasound information based on processed echo signals.

22. The ultrasound system of claim 21, wherein said switch network modulates said series of pulses to include at least two different pulse widths.

23. The ultrasound system of claim 21, wherein said switch network modulates said series of pulses to include a narrow first pulse having a first amplitude, a wider second pulse having a second amplitude and a narrow third pulse having a third amplitude, said transmitter controlling first, second and third pulse width in increments of one of 6.2 ns and greater than 6.2 ns.

24. The ultrasound system of claim 21, wherein said switch network drives each element within said array of elements with a different said series of pulses.

* * * * *